United States Patent [19]

Butter

[11] 3,979,472
[45] Sept. 7, 1976

[54] PROCESS FOR MANUFACTURING HYDROCARBONS

[75] Inventor: Stephen A. Butter, East Windsor, N.J.

[73] Assignee: Mobil Oil Corporation, New York, N.Y.

[22] Filed: Mar. 28, 1975

[21] Appl. No.: 563,241

[52] U.S. Cl. .................... 260/668 R; 252/455 Z; 260/673; 260/682
[51] Int. Cl.² .................................. C07C 1/20
[58] Field of Search ............ 260/668 R, 673, 682; 252/455 Z

[56] References Cited
UNITED STATES PATENTS

| | | | |
|---|---|---|---|
| 3,894,105 | 7/1975 | Chang et al. | 260/668 R |
| 3,894,106 | 7/1975 | Chang et al. | 260/668 R |
| 3,894,107 | 7/1975 | Butter et al. | 260/668 R |
| 3,899,544 | 8/1975 | Chang et al. | 260/668 C |
| 3,907,915 | 9/1975 | Chang et al. | 260/668 R |

*Primary Examiner*—C. Davis
*Attorney, Agent, or Firm*—Charles A. Huggett; Vincent J. Frilette

[57] ABSTRACT

A catalytic process, employing a novel catalyst, for converting lower monohydric alcohols and their ethers, especially methanol and dimethyl ether, to a hydrocarbon mixture mostly ethylene, propylene and mononuclear aromatics. The novel catalyst is a composite of antimony oxide and a crystalline aluminosilicate zeolite such as ZSM-5.

11 Claims, No Drawings

3,979,472

PROCESS FOR MANUFACTURING HYDROCARBONS

FIELD OF THE INVENTION

This invention is concerned with the manufacture of hydrocarbons from lower alcohols or their ethers. It is particularly concerned with the catalytic conversion of such alcohols and ethers to hydrocarbon mixtures rich in ethylene. In another aspect, this invention is concerned with a novel catalyst especially effective for the conversion of lower alcohols to ethylene and aromatic hydrocarbons.

DESCRIPTION OF PRIOR ART

A remarkable growth in the production of synthetic fibers, plastics and rubber has taken place in recent decades. This growth, to a very large extent, has been supported and encouraged by an expanding supply of inexpensive petrochemical raw materials such as ethylene, benzene, toluene, and xylenes. Side by side with this remarkable development, there has been an increasing demand for aromatic hydrocarbons for use as high octane gasoline components. Environmental factors which limit the lead content of gasoline are likely to aggravate the need for aromatics.

Burgeoning demand for olefins, particularly ethylene, and for aromatic hydrocarbons, has of course led to periods of shortage, either due to short supply of suitable feedstocks or to limited processing capacity. In any case, it would appear desirable to provide efficient means for converting raw materials other than petroleum to olefins and aromatic hydrocarbons.

Copending application Ser. No. 508,308, filed Sept. 23, 1974, (attorney's docket number Case 8487) discloses a catalyst comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight and discloses the conversion of aliphatic compounds, particularly hydrocarbons, both paraffins and olefins, by contact with the catalyst.

Copending application Ser. No. 508,307 filed Sept. 23, 1974, now U.S. Pat. No. 3,911,041, describes the conversion of methanol and of dimethyl ether to hydrocarbons when contacted with phosphorous-modified ZSM-5 type catalyst.

Copending application Ser. No. 508,306, filed Sept. 23, 1974, now U.S. Pat. No. 3,906,054, discloses a process for the alkylation of olefins employing, as a catalyst, a crystalline aluminosilicate zeolite having a silica to alumina ratio of at least about 12, a constraint index of about 1 to 12, and containing phosphorus incorporated with the crystal structure thereof in an amount of at least about 0.78 percent by weight.

Copending applications Ser. Nos. 387,222; 387,223; and 387,224, filed Aug. 9, 1973, now U.S. Pat. Nos. 3,894,106, 3,894,107 and 3,907,915, respectively, disclose the conversion of alcohols and/or ethers and/or carbonyls to higher carbon number hydrocarbons by contact with a catalyst comprising a crystalline aluminosilicate zeolite having a silica to alumina ratio of at least about 12 and a constraint index of about 1 to 12.

The conversion of methanol and dimethyl ether to hydrocarbons is described in copending U.S. Patent Application Ser. No. 508,307, filed Sept. 23, 1974.

A process for preparing attrition-resistant solid catalysts containing antimony oxide is described in U.S. Pat. No. 3,686,138, issued Aug. 22, 1972.

BRIEF SUMMARY OF THE INVENTION

In the present invention, lower monohydric alcohols having up to four carbon atoms, their ether derivatives, or mixtures of any of these are converted by contact at elevated temperatures with a novel catalyst, described below, to form hydrocarbon mixtures rich in light olefins, especially ethylene, and aromatic hydrocarbons. The novel catalyst utilized in this invention is a composite of antimony oxide and a porous inorganic oxide preferably of the crystalline aluminosilicate zeolite type as hereinafter described.

The alcohols may be manufactured from synthesis gas, i.e., a mixture of CO and $H_2$, from coal, or they may be produced by fermentation, or they may be manufactured from petroleum fraction in excess supply. The aromatic hydrocarbons produced may be used to blend with gasoline, or they may be separated and used as petrochemicals and as solvents. Thus, in one aspect, the present invention provides a novel means for producing hydrocarbon petrochemicals and fuels.

PREFERRED EMBODIMENTS

Any composition consisting essentially of one or more compounds having the empirical formula [ $(CH_2)n(CH_2)m$ ]$H_2O$ wherein $n = 1$ to 4 and $m = 0$ to 4 may be used as feed to the process of this invention. Thus, methanol, ethanol, n-propanol, isopropanol, n-butanol, sec-butanol and isobutanol may be used either alone or in admixture with one another, or in admixture with the above alcohols. Likewise, mixed ethers derived from these alcohols, such as methyl-ethyl ether, may be likewise used. It will be noted that all of the compounds indicated have the empirical formula above described. Particularly preferred feeds are methanol, dimethyl ether and mixtures thereof.

The preferred catalysts of this invention comprise composites of antimony oxide and a crystalline aluminosilicate zeolite more fully described below. The ratio of antimony oxide to crystalline aluminosilicate zeolite may be from about 0.01 to about 0.50, and preferably from about 0.03 to about 0.30. The ratio in all cases is by weight of $Sb_2O_3$ to dry zeolite. The antimony oxide may be present as $Sb_2O_3$, $Sb_2O_4$, $Sb_2O_5$ or mixtures thereof with or without metallic antimony or other antimony compounds being present. In all instances, regardless of the particular state of oxidation of the antimony, its content vis a vis the zeolite is computed as if it were present as $Sb_2O_3$.

The catalysts of this invention may be a physical mixture of an antimony compound, preferably an oxide such as $Sb_2O_3$, $Sb_2O_4$, or $Sb_2O_5$, with the zeolite powder; or, the product formed by impregnation of the zeolite powder or pellets with one or more organic or inorganic antimony compound; or the product formed by any known catalyst preparation procedure that results in an intimate mixture. Antimony derivatives which may be used include: the hydrides $SbH_3$; the halides $MX_3$, $MX_5$ (M = Sb, X = F, Cl, Br, I); organic alkyl and aryl stibines and their oxides $R_3Sb$, $R_5Sb$, $R_xSb=O$ (R=alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO . OH$, all with R and X defined as above noted. Also included are organic ethers such as R$_2$SbOSbR$_2$; esters and alcoholates such as Sb(OOCH$_3$)$_3$, Sb(OC$_4$H$_9$)$_3$, Sb(OC$_2$H$_5$)$_3$, Sb(OCH$_3$)$_3$; and antimonyl salts as (SbO)SO$_4$, (SbO)NO$_3$, K(SbO)C$_4$H$_4$O$_6$, NaSbO$_2$ . 3H$_2$O. Binders such as clays, silica, or other inorganic oxides may be used. When such are used, the total catalyst composition should preferably contain at least 50 percent by weight of crystalline aluminosilicate zeolite. When the catalyst composition has the desired physical form, it is dried and then calcined at a temperature of about 200°C to about 600°C, preferably in an oxidizing atmosphere such as air. In some cases, calcining in a reducing atmosphere may be found preferable, in which case the calcining temperature should not exceed about 550°C.

The catalysts referred to herein utilize members of a special class of zeolites exhibiting some unusual properties. These zeolites by themselves induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000°F for at least 15 minutes. The zeolite is then flushed with helium and the temperature adjusted between 550°F and 950°F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those which employ a zeolite havving a constraint index from 1.0 to 12.0. Constraint Index (CI) values for some typical zeolites including some not within the scope of this invention are:

| CAS | C.I. |
| --- | --- |
| ZSM-5 | 8.3 |
| ZSM-11 | 8.7 |
| TMA Offretite | 3.7 |
| ZSM-12 | 2 |
| Beta | 0.6 |
| ZSM-4 (Omega) | 0.5 |
| H-Zeolon | 0.5 |
| REY | 0.4 |
| Amorphous Silica-alumina | 0.6 |
| Erionite | 38 |

The above described constraint Index is an important, and even critical, definition of those zeolites which are useful as catalysts components. The very nature of this parameter, however, and the recited technique by which it is determined, however, admit of the possibility that a given zeolite can be tested under somewhat different conditions and thereby have different constraint indexes. Constrainst Index seems to vary somewhat whith severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property, "the Constraint Index," as used in this invention, is an inclusive rather than an exclusive value. That is, a zeolite, if tested by any combination of conditions within the limits set forth herein above and found to have a constraint index of 1 to 12, is included in the instant catalyst definition regardless that the same identical zeolite tested under other conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application, Ser. No. 358,192, filed May 7, 1973, and now abandoned, the entire contents of which are incorporated herein by reference, describes a zeolite composition, and a method of making such, designated as ZSM-21 which is useful in this invention. Recent evidence has been adduced which suggests that this composition may be composed of at least two (2) different zeolites, one or both of which are the effective material insofar as the catalysis of this invention is concerned. Either or all of these zeolites is considered to be within the scope of this invention.

The specific zeolites described, when prepared in the presence of organic cations, are substantially catalytically inactive, possible because the intracrystalline free space is occupied by organic cations from the forming solution. They may be activated by heating in an inert atmosphere at 1000°F for 1 hour, for example, followed by base exchange with ammonium salts followed by calcination at 1000°F in air. The presence of organic cations in the forming solution may not be absolutely essential to the formation of this special type zeolite; however, the presence of these cations does appear to favor its formation. More generally, it is desirable to activate this type zeolite by base exchange with ammonium salts followed by calcination in air at about 1000°F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, and ZSM-21, with ZSM-5 particularly preferred.

The zeolites used as catalyst components in this invention may be in the hydrogen form or they may be base exchanged or impregnated to contain ammonium or a metal cation complement. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be large inactive.

In a preferred aspect of this invention, the zeolites useful herein are selected as those having a crystal framework density, in the dry hydrogen form, of not substantially below about 1.6 grams per cubic centimeter. It has been found that zeolites which satisfy all three of the criteria are most desired. Therefore, the preferred zeolites are those comprising zeolites having a constraint index as defined above of about 1 to 12, a silica to alumina ratio of at least about 12 and a dried crystal density in the hydrogen form of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In the process of this invention, the feed consisting essentially of one or more of the lower alcohols or ethers derived therefrom is contacted with the above described catalyst at a temperature of about 250°C to about 700°C, and preferably about 350°C to 500°C; a contact time equivalent to or the same as a weight hourly space velocity (WHSV) of about 0.5 to 50, preferably about 1.0 to 10.0, it being understood that WHSV signifies pounds of feed per pound of catalyst per hour; and at an absolute pressure of about 0.2 to 30 atmospheres. The catalyst may be in the form of fixed bed, fixed fluid bed, or it may be of the transport bed type.

The product stream in the process of this invention contains steam and a hydrocarbon mixture particularly rich in the light olefins, ethylene and propylene, and aromatic hydrocarbons.

Generally, a major fraction of the total olefins, calculated on a mol basis, is ethylene plus propylene; and a major fraction of these two olefins is ethylene. The predominant aromatic hydrocarbons are monocyclic hydrocarbons such as benzene, toluene and xylene. Thus, the predominant hydrocarbons are all valuable petrochemicals. The steam and hydrocarbons are separated from one another by methods well known in the art. The particular proportions of olefins and aromatic hydrocarbons that are produced may be varied by varying the ratio of antimony oxide to crystalline aluminosilicate, higher antimony oxide contents favoring olefin formation. The proportions also may be varied by selecting reaction conditions within the purview specified above, olefins being favored by lower temperatures and in general by less severe convversion conditions. Thus, it is a feature of this invention that the product mix can be easily varied to suit changes of demand.

Catalyst deactivated by coke deposited during the process may be reactivated by calcining in air, for example by calcining at 500°C for about 20 hours. Operation of the process of this invention in the presence of added hydrogen may sometimes retard aging.

It is not fully understood why the composite catalyst of this invention produces such a desirable spectrum of products. Nonetheless, the conversion of a single carbon feed, such as methanol, or ite ether, with such high selectivity to two and three carbon olefins, particularly ethylene, and conjunctly to monocyclic aromatics, is surprising.

The following examples illustrate the practice of this invention without being limiting on the scope thereof. Parts and percentages are by weight unless expressly stated to be on some other basis.

EXAMPLES

EXAMPLE 1

6.5 grams of antimony trimethoxide $Sb(CH_3O)_3$ dissolved in 75 cc of para-xylene was refluxed with 10 grams of H-ZSM-5 for 16 hours. The mixture was cooled, filtered, and the filter cake washed with 100 cc of toluene, then 100 cc of methanol, than 100 cc of pentane, after which it was dried in air. The solids were then vacuum dried at 115°C for 3 hours, and formed into pellets without binder. The pellets were then calcined in air at 300°C for 1 hour. The catalyst contained 24% antimony as $Sb_2O_3$.

EXAMPLE 2

5.0 grams of the catalyst prepared in Example 1 was placed in a catalytic reactor. It was heated to 400°C and 13.2 cc of methanol was passed over it in 1 hour. Recovered products consisted of 5.9 grams aqueous liquid, 1.2 grams organic liquid, 1.4 grams liquified hydrocarbon gas and 1880 cc of dry gas (hydrogen, methane, ethane and carbon oxides), accounting for 96 weight percent of the alcohol charged.

A detailed analysis of the recovered product showed that substantially all of the methanol charged was converted to hydrocarbon. About 23% of the hydrocarbon product consisted of mononuclear aromatics, mostly xylenes; about 25% was ethylene and about 18% propylene.

EXAMPLES 3-8

13.4 cc per hour of methanol was passed over 4.4 grams of a fresh portion of the same catalyst used in Example 2 in a series of experiments at different temperatures from 300°C to 500°C. The products were analyzed with the results shown in Table 1, under Examples 3-7, inclusive. The catalyst, used in Example 7 at 500°C was found to be partially deactivated. It was calcined in air at 500°C for 18 hours, after which it was used to convert methanol. The results are shown in Table 1 under Example 8.

TABLE 1

| Example Number | 3 | 4 | 5 | 6 | 7 | 8 |
|---|---|---|---|---|---|---|
| Temp. °C. | 300 | 350 | 400 | 450 | 500 | 500 |
| Aliphatic Wt. % (1) | | | | | | |
| $H_2$ | .05 | .34 | .81 | 2.55 | 2.76 | 2.39 |
| CO | .86 | 1.70 | 1.86 | 12.01 | 19.78 | 17.44 |
| $CO_2$ | .20 | .75 | .78 | 6.45 | 9.11 | 6.09 |
| $CH_4$ | .58 | 1.07 | 2.93 | 14.59 | 44.71 | 24.49 |
| $C_2H_6$ | .23 | .44 | .78 | .98 | 1.38 | .83 |
| $C_2H_4$ | 35.90 | 27.05 | 24.15 | 18.83 | 10.12 | 11.72 |
| $C_3H_8$ | 4.55 | 3.32 | 3.07 | .96 | .25 | .38 |
| $C_3H_6$ | 36.92 | 29.79 | 20.43 | 12.61 | 6.31 | 5.99 |
| $C_4H_{10}$ | 4.24 | 2.11 | 2.24 | .60 | .21 | .34 |
| $C_4H_8$ | 13.55 | 10.18 | 9.59 | 5.32 | 4.03 | 2.42 |
| $C_5$ | 2.92 | 3.21 | 4.49 | 2.94 | 1.32 | 2.53 |
| $C_6$ | 0 | 1.14 | 3.56 | 1.38 | 0 | .99 |
| $C_{7+}$ | 0 | 4.24 | 3.89 | 1.13 | 0 | .71 |
| Aromatic Wt. % (1) | | | | | | |
| Benzene | 0 | .37 | .63 | .43 | 0 | .58 |
| Toluene | 0 | 1.77 | 2.20 | 2.03 | 0 | 3.15 |
| Xylenes | 0 | 8.61 | 12.81 | 10.06 | 0 | 11.31 |
| $ArC_9$ | 0 | 2.50 | 3.77 | 4.32 | 0 | 4.73 |
| $ArC_{10+}$ | 0 | 1.41 | 2.00 | 2.83 | 0 | 3.91 |
| Total Product Yield | 7.47 | 19.17 | 39.92 | 38.45 | 7.56 | 41.41 |

TABLE 1-continued

| Example Number | 3 | 4 | 5 | 6 | 7 | 8 |
|---|---|---|---|---|---|---|
| MeOMe | 50.07 | 32.30 | 3.56 | 8.17 | 44.83 | 5.65 |
| MeOH | 13.90 | 13.84 | 6.33 | 9.09 | 22.60 | 8.46 |
| $H_2O$ | 28.56 | 34.70 | 50.19 | 44.29 | 25.01 | 44.48 |
| Conversion % | | | | | | |
| | 86.12 | 86.16 | 93.67 | 90.91 | 77.40 | 91.54 |
| Material Bal. % | | | | | | |
| | 99.49 | 100.48 | 96.32 | 94.42 | 94.44 | 96.41 |

(1) Based on hydrocarbon portion only (excludes MeOh, Me$_2$O, H$_2$O).

What is claimed is:

1. A process for producing hydrocarbons which comprises: contacting, under conversion conditions, a feed consisting essentially of one or more lower monohydric alcohol having up to four carbon atoms, the ethers derived therefrom, or mixtures of said alcohols and ethers, with a catalyst comprising an intimate admixture of an oxide of antimony and a crystalline aluminosilicate zeolite having a silica to alumina ratio of at least about 12 and a constraint index from 1 to 12, said antimony oxide constituting at least 1% by weight of said admixture, whereby is formed a mixture comprising light olefins, monocyclic aromatic hydrocarbons, and water; and, recovering said hydrocarbons.

2. The process of claim 1 wherein said conversion conditions include a space velocity of about 0.5 to 50 WHSV, a temperature of about 300°C to about 550°C, and a pressure of about 0.2 to 30 atmospheres.

3. The process of claim 2 wherein said feed is methanol, dimethyl ether or mixtures thereof.

4. The process of claim 1 wherein said crystalline aluminosilicate zeolite is HZSM-5.

5. The process of claim 1 wherein the ratio of antimony oxide to crystalline aluminosilicate zeolite is from about 0.01 to about 0.50.

6. The process of claim 1 wherein the ratio of antimony oxide to crystalline aluminosilicate zeolite is from about 0.03 to 0.30.

7. The process of claim 6 wherein said feed consists essentially of methanol, dimethyl ether or mixtures thereof.

8. A novel catalyst composition useful for converting lower alcohols to petrochemical-type hydrocarbons, which comprises a composite of antimony oxide and a crystalline aluminosilicate zeolite having a silica to alumina ratio of at least about 12, a constraint index of from 1 to 12, and a dried crystal density in the hydrogen form not less than about 1.6 grams per cubic centimeter, wherein said composite contains at least 1% by weight of antimony oxide.

9. A novel catalyst composition as described in claim 8, wherein said zeolite is HZSM-5 and wherein the ratio of said antimony oxide to crystalline aluminosilicate is from about 0.01 to 0.50.

10. A method for preparing a catalytic composition useful in the conversion of alcohols to hydrocarbon mixtures, which comprises: heating together a solution of antimony trimethoxide and a crystalline aluminosilicate zeolite for a time sufficient to form an intimate mixture of said zeolite and an insoluble antimony compound; recovering said intimate mixture; and calcining said recovered mixture in air.

11. The method of claim 10 wherein said crystalline aluminosilicate zeolite is H-ZSM-5.

* * * * *